(12) United States Patent
Stchur et al.

(10) Patent No.: US 11,813,171 B2
(45) Date of Patent: Nov. 14, 2023

(54) OSTEOTOME AND SHOULDER ARTHROPLASTY SYSTEM

(71) Applicant: Sure Orthopedics LLC, Sarasota, FL (US)

(72) Inventors: Robert Patrick Stchur, Punta Gorda, FL (US); John D. Kuczynski, Sarasota, FL (US)

(73) Assignee: Sure Orthopedics LLC, Sarasota, FL (US)

( * ) Notice: Subject to any disclaimer, the term of this patent is extended or adjusted under 35 U.S.C. 154(b) by 191 days.

(21) Appl. No.: 16/796,029

(22) Filed: Feb. 20, 2020

(65) Prior Publication Data

US 2020/0261247 A1 Aug. 20, 2020

Related U.S. Application Data

(60) Provisional application No. 62/918,947, filed on Feb. 20, 2019.

(51) Int. Cl.
| | |
|---|---|
| *A61F 2/46* | (2006.01) |
| *A61F 2/40* | (2006.01) |
| *A61F 2/08* | (2006.01) |
| *A61F 2/30* | (2006.01) |
| *A61B 17/15* | (2006.01) |
| *A61B 17/16* | (2006.01) |

(52) U.S. Cl.
CPC ............ *A61F 2/4014* (2013.01); *A61B 17/15* (2013.01); *A61B 17/1615* (2013.01); *A61B 17/1633* (2013.01); *A61F 2/0811* (2013.01); *A61F 2/30771* (2013.01); *A61F 2/4059* (2013.01); *A61F 2/4607* (2013.01); *A61F 2/4612* (2013.01); *A61F 2002/0829* (2013.01); *A61F 2002/0864* (2013.01); *A61F 2002/30242* (2013.01); *A61F 2002/30405* (2013.01); *A61F 2002/30433* (2013.01); *A61F 2002/30654* (2013.01); *A61F 2002/30836* (2013.01); *A61F 2002/30845* (2013.01); *A61F 2002/4022* (2013.01); *A61F 2002/4051* (2013.01); *A61F 2002/4062* (2013.01); *A61F 2002/4085* (2013.01); *A61F 2002/4619* (2013.01)

(58) Field of Classification Search
CPC .................. A61F 2/4603; A61F 2/4612; A61F 2002/4619; A61B 17/151; A61B 17/152; A61B 17/1659; A61B 17/1684
See application file for complete search history.

(56) References Cited

U.S. PATENT DOCUMENTS

| | | | | |
|---|---|---|---|---|
| 5,282,865 A | * | 2/1994 | Dong | A61F 2/40 623/19.14 |
| 5,507,817 A | * | 4/1996 | Craig | A61F 2/4014 623/20.11 |
| 5,702,486 A | * | 12/1997 | Craig | A61F 2/4059 623/19.14 |
| 5,944,758 A | * | 8/1999 | Mansat | A61F 2/40 623/19.14 |
| 6,264,657 B1 | * | 7/2001 | Urbahns | A61B 17/1671 606/279 |

(Continued)

*Primary Examiner* — Anu Ramana
(74) *Attorney, Agent, or Firm* — Kim IP Law Group LLC

(57) ABSTRACT

An osteotome having a shaft assembly that includes a guide extending in a longitudinal direction of the shaft assembly, and a blade adjacent the guide and extending in the longitudinal direction of the shaft assembly.

19 Claims, 14 Drawing Sheets

(56) References Cited

U.S. PATENT DOCUMENTS

| | | | | |
|---|---|---|---|---|
| 6,790,234 | B1* | 9/2004 | Frankle | A61F 2/40 623/19.12 |
| 7,556,652 | B2* | 7/2009 | Angibaud | A61F 2/4059 623/19.14 |
| 7,578,820 | B2* | 8/2009 | Moore | A61F 2/4611 600/203 |
| 11,058,550 | B2* | 7/2021 | LaNeve | A61F 2/30771 |
| 2002/0133153 | A1* | 9/2002 | Hyde, Jr. | A61B 17/1684 606/53 |
| 2005/0049623 | A1* | 3/2005 | Moore | A61B 17/1631 606/170 |
| 2005/0177241 | A1* | 8/2005 | Angibaud | A61F 2/4014 623/19.14 |
| 2006/0200249 | A1* | 9/2006 | Beguin | A61F 2/4014 623/19.14 |
| 2013/0197652 | A1* | 8/2013 | Ekelund | A61F 2/30728 623/19.14 |
| 2013/0261754 | A1* | 10/2013 | Anthony | A61F 2/4612 623/19.14 |
| 2015/0127104 | A1* | 5/2015 | Levy | A61F 2/4003 623/14.12 |
| 2016/0324648 | A1* | 11/2016 | Hodorek | A61F 2/4059 |

* cited by examiner

SECTION A-A

SECTION A-A

OSTEOTOME AND SHOULDER ARTHROPLASTY SYSTEM

BACKGROUND OF THE DISCLOSURE

The exemplary embodiments of the subject disclosure relate generally to a surgical osteotome. The presently disclosed osteotome can be used, for example, to remove bone ingrowth that has occurred over time on an implant that is now being removed or adjusted during revision surgery. Embodiments of the presently disclosed subject matter also relate to orthopedic implants (e.g. a humeral stem) adapted to be used with the presently disclosed osteotomes.

SUMMARY OF THE DISCLOSURE

In accordance with an exemplary embodiment, the subject disclosure provides an osteotome that includes a shaft assembly having a guide extending in a longitudinal direction of the shaft assembly, and a blade adjacent the guide and extending in the longitudinal direction of the shaft assembly. The blade includes a distally facing cutting edge.

In exemplary embodiments of the subject disclosure, the guide, which can be an elongated guide, is a substantially cylindrical or a substantially annular guide. According to exemplary embodiments, the guide has a longitudinal cross-section of a circle, oval, square, rectangle, trapezoid, triangle, or curve.

The blade can be an elongated blade and can have a longitudinal cross-section of, for example, a curve, or can be substantially U-shaped, substantially V-shaped, or substantially trapezoidal shaped. In an exemplary embodiment, the blade has a first planar section adjacent the guide, a second planar section extending from the first planar section, and a third planar section extending from the first planar section. The second and third planar sections are, in certain embodiments, adjacent opposite sides of the guide. For example, the second planar section and/or the third planar section can extend from the first planar section about 90° to about 180°.

According to exemplary embodiments, the osteotome includes a handle connected to a proximal end of the shaft assembly. The handle can include a striking surface, such as a substantially planar proximally facing striking surface. The handle can further include an internal cavity, in which the guide includes a through hole extending along a longitudinal direction of the guide and in fluid communication with the internal cavity.

In another exemplary embodiment, the subject disclosure provides an orthopedic implant that includes a stem having a groove extending along a longitudinal direction of the stem (e.g., along a majority of the stem length). The stem can be e.g., a humeral stem of a shoulder implant or a stem of any orthopedic implant, such as a hip implant.

In another exemplary embodiment, the subject disclosure provides a shoulder arthroplasty system that includes a shoulder implant and an osteotome, as described herein. The shoulder implant includes a humeral stem having a groove extending along a longitudinal length of the humeral stem, and a perimeter wall section adjacent the groove. The groove can be complementary shaped to the guide for receiving the guide therein.

BRIEF DESCRIPTION OF THE SEVERAL VIEWS OF THE DRAWINGS

The following detailed description of the exemplary embodiments of the subject disclosure will be better understood when read in conjunction with the appended drawings. For the purpose of illustrating the present disclosure, there is shown in the drawings exemplary embodiments. It should be understood, however, that the subject application is not limited to the precise arrangements and instrumentalities shown.

DETAILED DESCRIPTION OF THE DISCLOSURE

Figure 1:
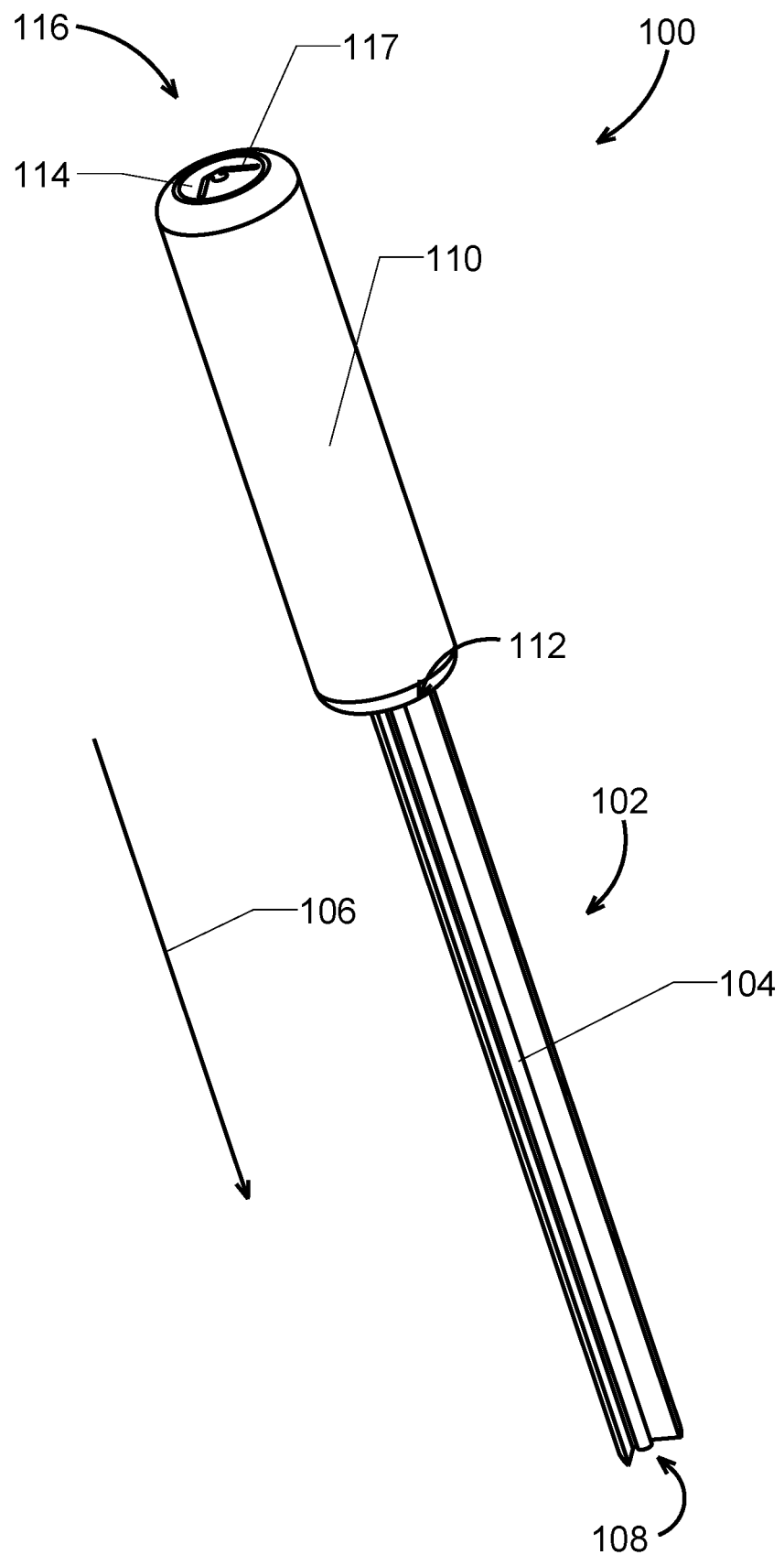
FIG. 1 is a perspective view of an osteotome in accordance with an exemplary embodiment of the subject disclosure.

Reference will now be made in detail to the exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. In reference to the disclosure herein, for purposes of convenience and clarity only, directional terms such as upper, lower, top, bottom, above, below and diagonal, are used with respect to the accompanying drawings. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art.

As used herein, the term "adjacent" refers to being near or adjoining. Adjacent components (which can be integral or separate) can be spaced apart from one another, or can be in actual or direct contact with one another (i.e., directly adjacent).

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Figure 2A:
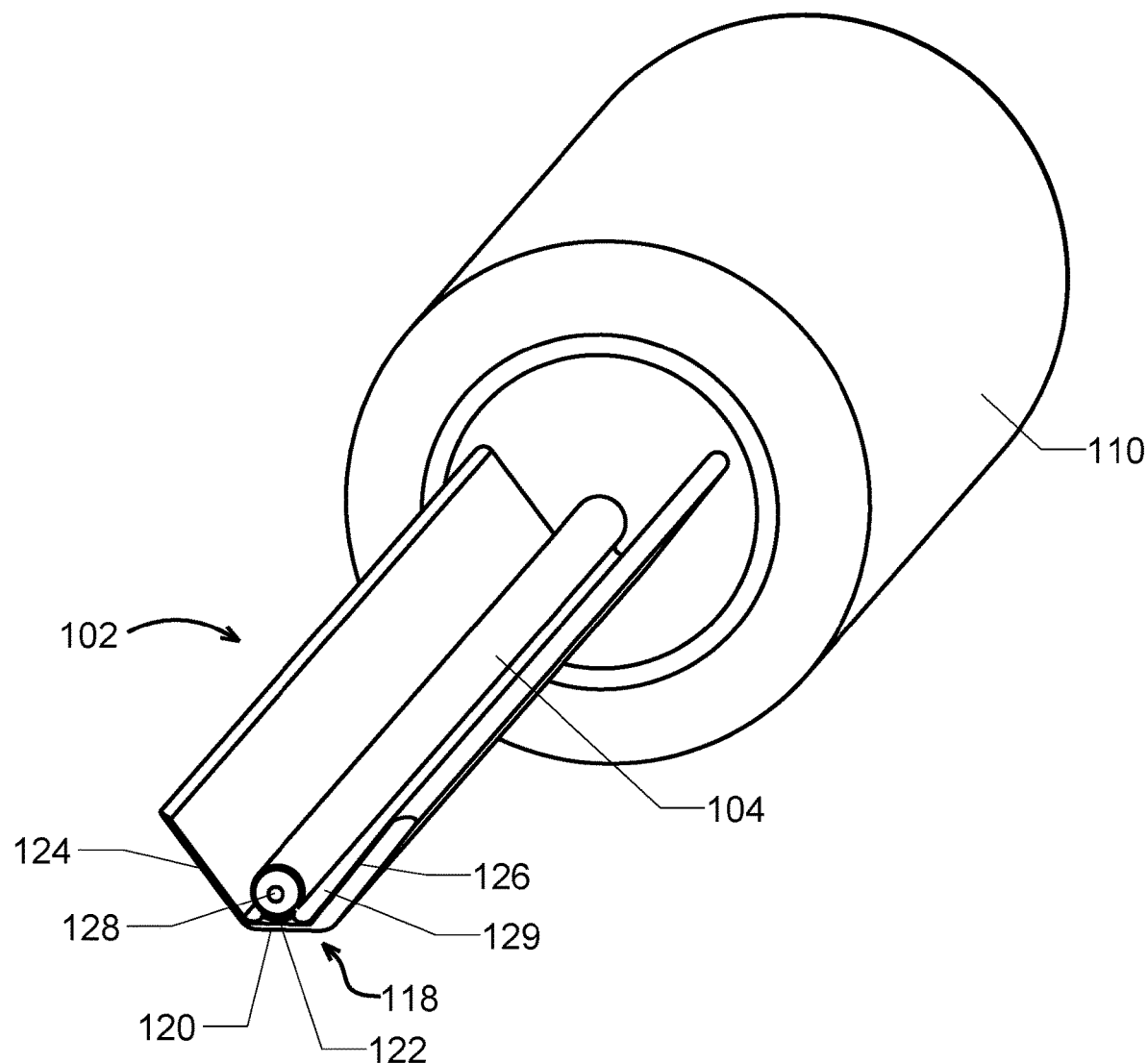
FIG. 2A is another perspective view of the osteotome of FIG. 1.
Figure 2B:
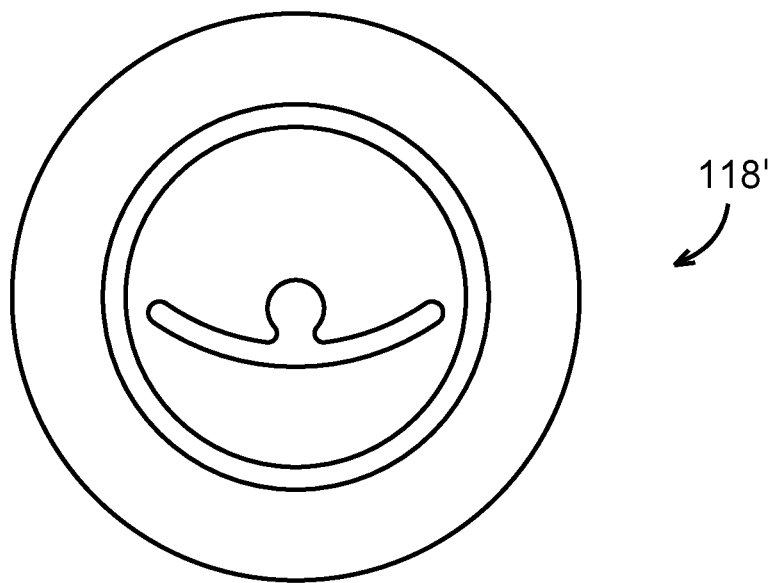
FIGS. 2B-2J illustrate osteotomes according to exemplary, alternate embodiments of the instant disclosure.
Figure 2C:
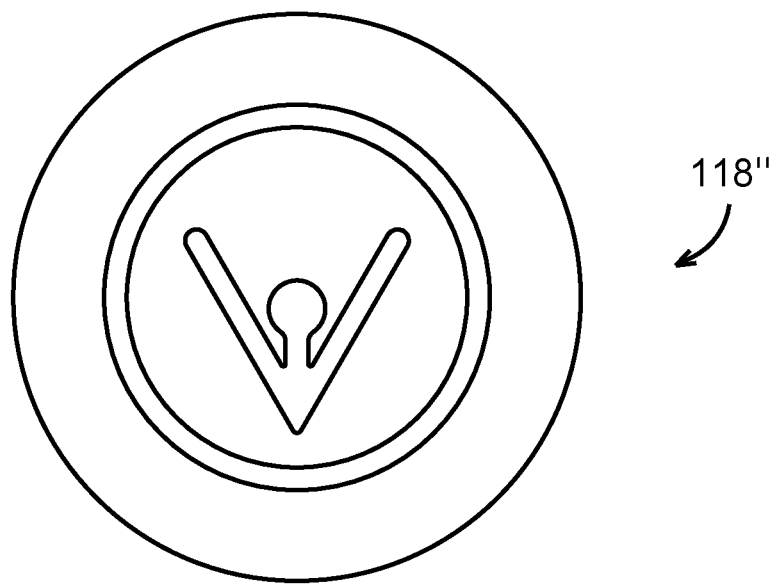
Figure 2D:
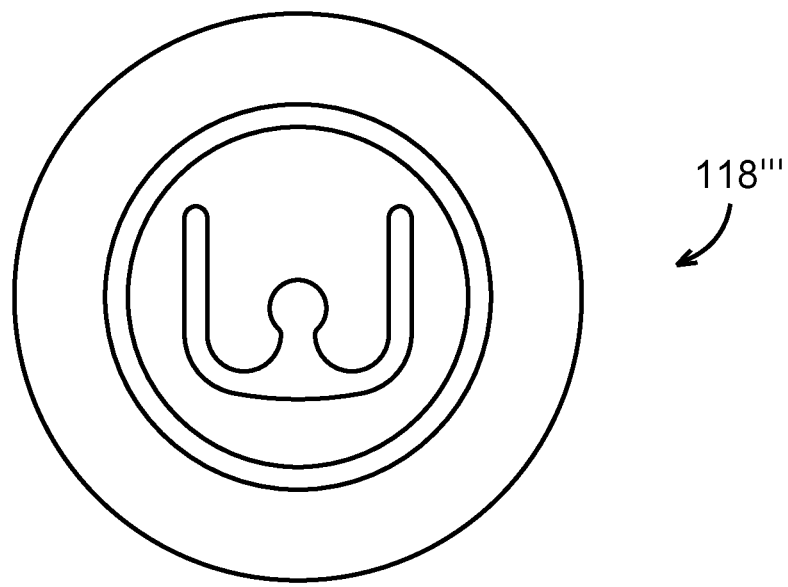
Figure 2E:
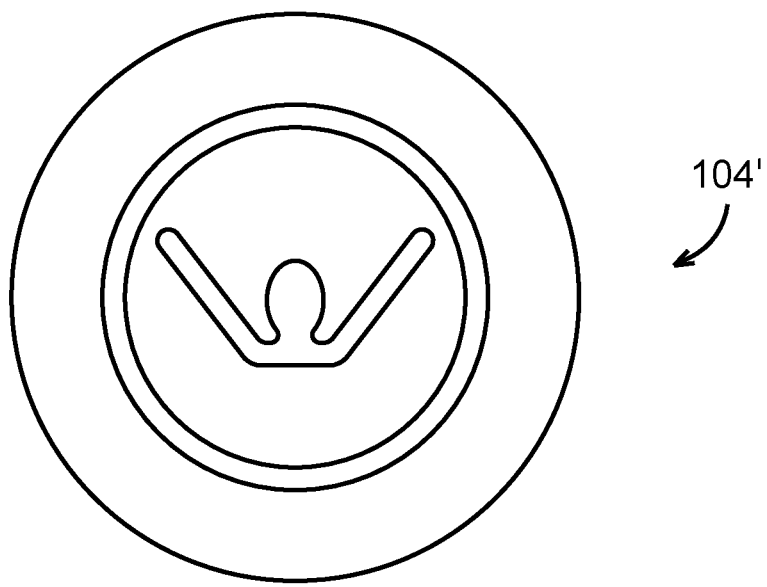
Figure 2F:
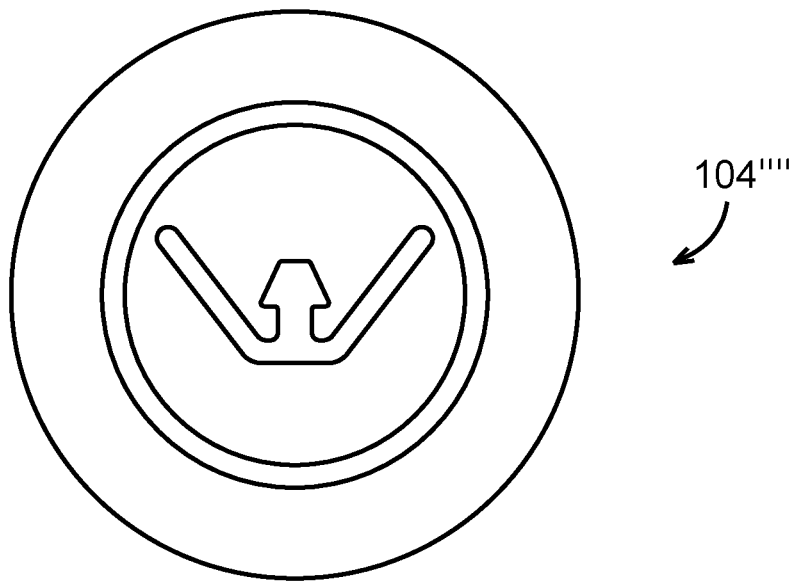
Figure 2G:
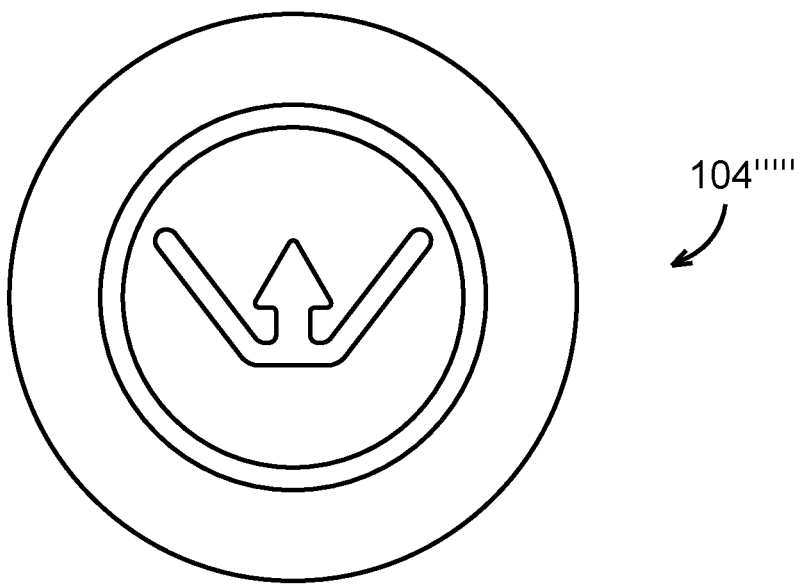
Figure 2H:
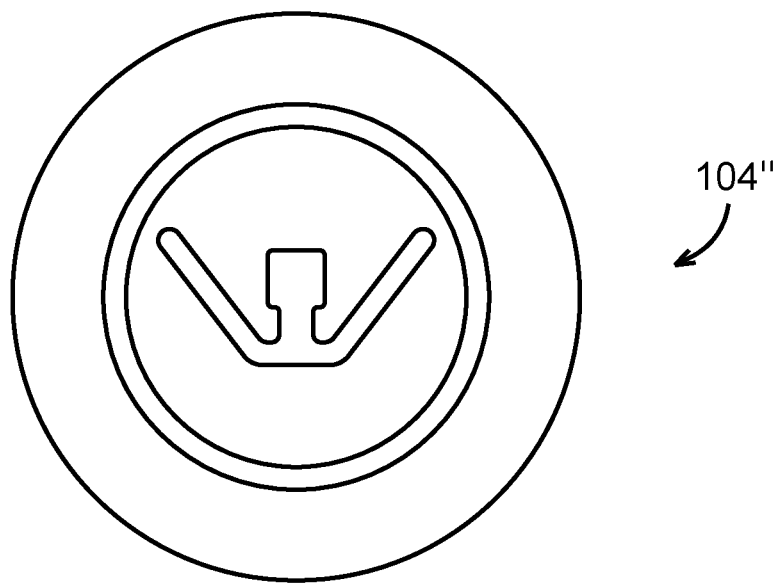
Figure 2I:
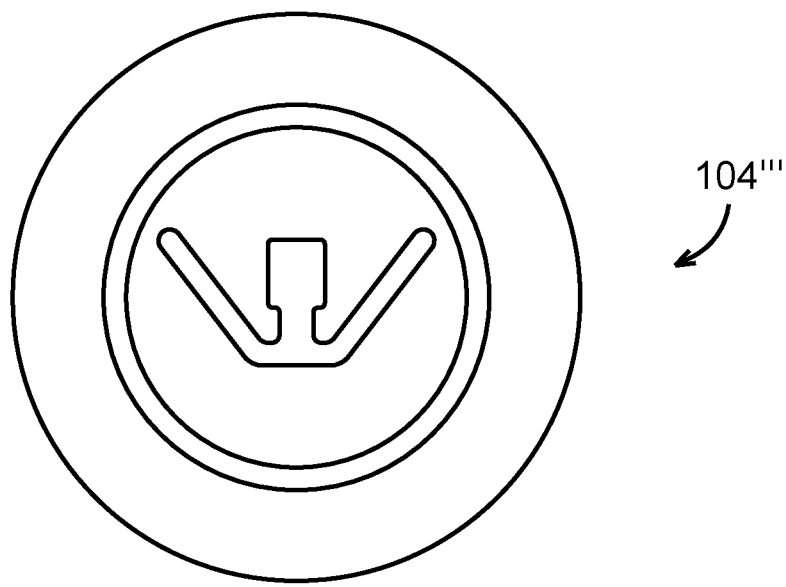
Figure 2J:
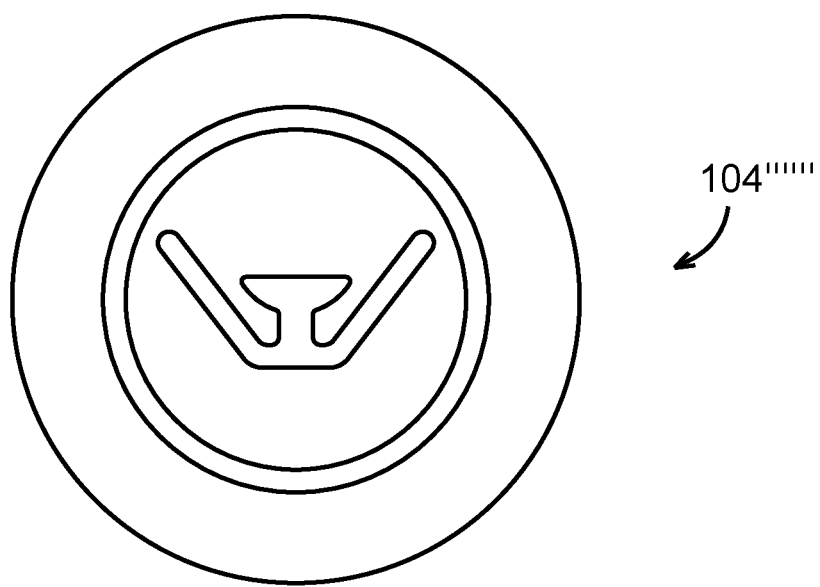
Figure 3:
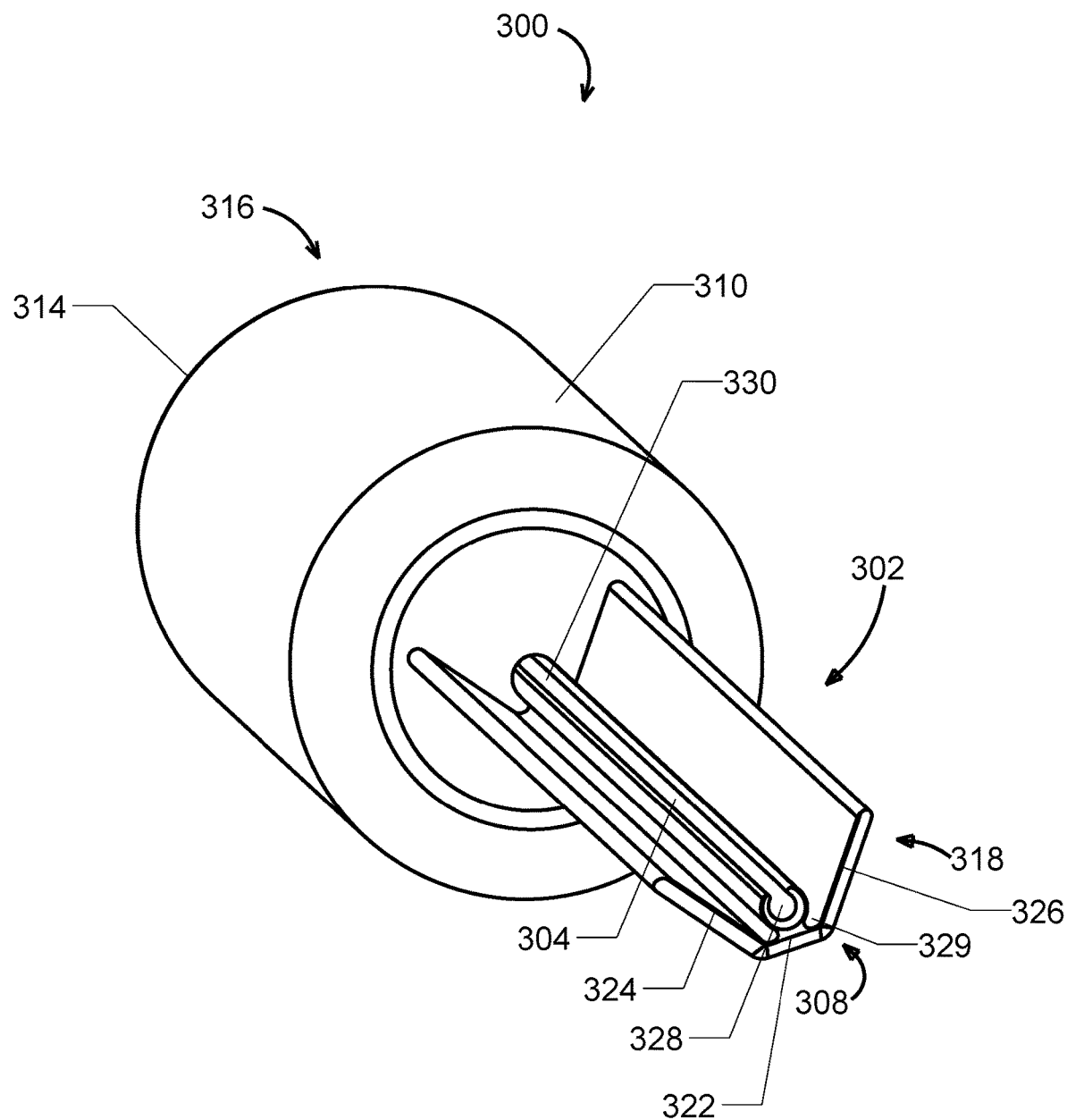
FIG. 3 is a perspective view of an osteotome in accordance with another exemplary embodiment of the subject disclosure.

Referring now to the drawings, FIGS. 1-2J disclose osteotomes according to exemplary embodiments of the subject disclosure. The osteotome 100 includes a shaft assembly 102 that includes a guide 104 that extends in a longitudinal direction 106 of the shaft assembly to a distal end 108 of the osteotome. A handle 110 is secured to a proximal end 112 the shaft assembly 102. The handle includes a striking surface 114 defining a proximal end 116 of the osteotome 100. The striking surface 114 can be, in certain exemplary embodiments, a planar or substantially planar proximally facing striking surface 115 (FIG. 9), and can optionally display an indicia 117 of the shape of the outer perimeter of the shaft assembly 102, for purposes of identification and orientation of the osteotome during use.

The handle 110 according to this exemplary embodiment has a circular cross-sectional shape, though other shapes could be provided that allow a user to manually grasp the handle to manipulate and control the osteotome 100. As explained further below, the handle 110 can, in certain exemplary embodiments, be provided with an enclosed or partially enclosed internal cavity 331 (FIG. 5A) to collect bone removed by the osteotome during use.

As shown best in FIG. 2A, the osteotome includes a blade 118 that includes a distally facing cutting edge 120 adapted to cut bone to facilitate e.g., removal of an orthopedic implant from bone in a patient. In this exemplary embodiment, the blade 118 is an elongated blade and includes a first planar section 122 directly adjacent of the guide 104. The blade 118 further includes a second planar section 126 extending from an end of the first planar section 122, and a third planar section 126 extending from an opposite end of the first planar section, both the second and third planar sections located adjacent to the guide 104.

As shown in FIG. 2A, the elongated blade 118 has a longitudinal cross-section that is substantially trapezoidal shaped, though other configurations could be provided. For example, according to the alternative embodiments disclosed in FIGS. 2B-2D, the elongated blade can have a curved cross-sectional shape blade 118' (FIG. 2B), a substantially V-shaped cross-sectional shape blade 118" (FIG. 2C), or substantially U-shaped cross-sectional shape blade 118''' (FIG. 2D). The cross-sectional shape of the blade can be provided to correspond to the contours of a perimeter wall section of an implant (e.g., first perimeter wall section 570, discussed below), particularly a perimeter wall section of an implant that is located adjacent a groove of the implant, as will be discussed in greater detail below.

The distal end 128 of the guide 104 can be defined by a pointed or conical end according to exemplary embodiments, to allow the osteotome to shear any bone ingrowth from surfaces of the orthopedic implant which the distal end of the guide engages, such as bone ingrowth that may occur in a groove of an orthopedic implant, as will be discussed below.

FIGS. 3, 4A, 4B, 5A and 5B depict an osteotome 300 according to an alternative, exemplary embodiment of the subject disclosure. Osteotome 300 is similar to osteotome 100, with like reference numbers used throughout these drawings to refer to the same or like features and the accompanying description of these features.

The osteotome 300 includes a shaft assembly 302 that includes a substantially annular or annular (e.g., cannulated) guide 304, 304' that extends to a distal end 308 of the osteotome. A handle 310 is secured to a proximal end 312 the shaft assembly 302, with a striking surface 314 defining a proximal end 316 of the osteotome 300. In this particular embodiment, the handle 310 contains an internal cavity 331 enclosed or partially enclosed by the outer perimeter of the handle 310.

A blade 318 with a cutting edge 320 is provided directly adjacent a distal end 328 of the guide 304. The blade 318 is an elongated blade and oriented similar to blade 118, and includes a first planar section 322, second planar section 324, and a third planar section 326 of the blade. In this particular embodiment, the second planar section 324 and the third planar section 326 extend at an equal angle from the first planar section, though they can extend at different angles in alternative embodiments.

Figure 4A:
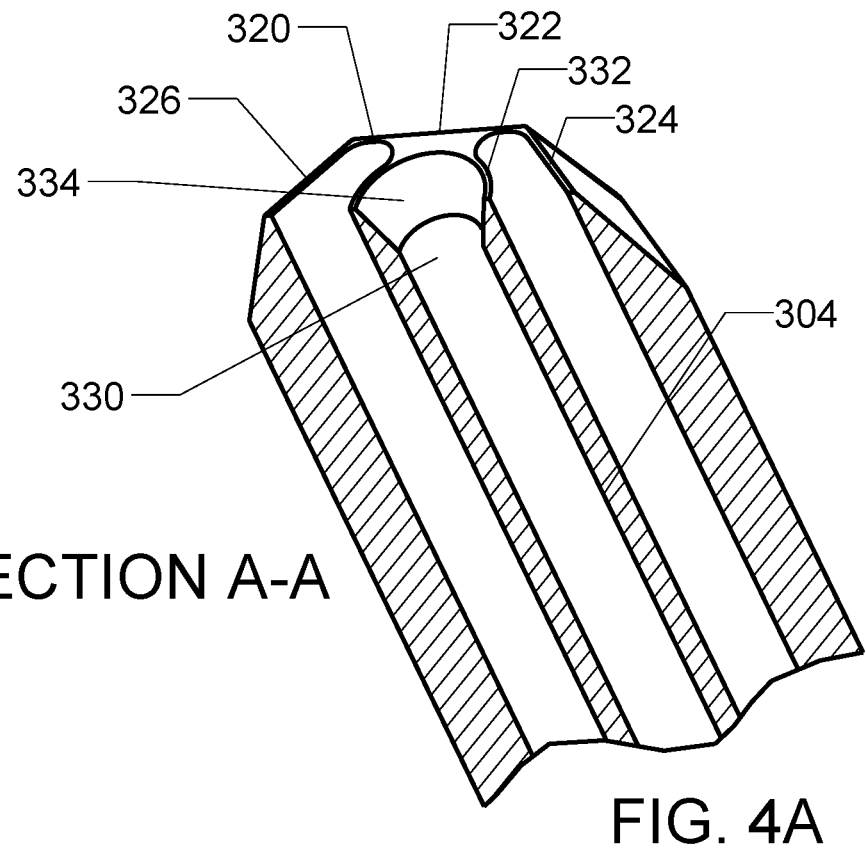
FIG. 4A is a perspective cross-sectional view.
Figure 4B:
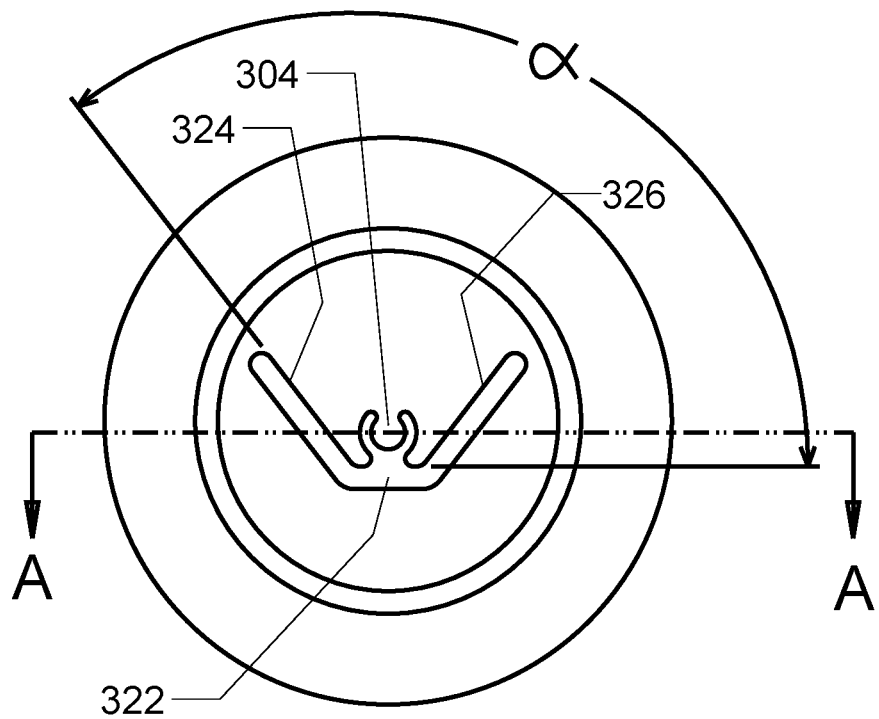
FIG. 4B is a bottom view of the osteotome of FIG. 3.

As shown best in FIG. 4B, the second planar section 324 and/or the third planar section 326 extend from the first planar section 322 at an angle, a, of about 125° to about 135°, or from about 128° to about 132° (e.g., 130°). Alternatively, the second planar section 324 and the third planar section 326 of the blade can extend from the first planar section 322, at an angle from about 90° to about 180°, or from about 110° to about 150° (e.g., 110°, 111°, 112°, 113°, 114°, 115°, 116°, 117°, 118°, 119°, 120°, 121°, 122°, 123°, 124°, 125°, 126°, 127°, 128°, 129°, 130°, 131°, 132°, 133°, 134°, 135°, 136°, 137°, 138°, 139°, 140°, 141°, 142°, 143°, 144°, 145°, 146°, 147°, 148°, 149°, or) 150°.

The substantially annular guide 304 shown in FIGS. 4A and 4B contains an orifice 330. The guide can include a distally facing cutting edge 332 to remove bone ingrowth from a groove or recess shaped complementary to the guide 304. A proximal end of the guide extends into the internal cavity of the handle 310 through a through hole such that the internal cavity 331 is in fluid communication with the orifice 330 of the guide and bone material removed within the orifice during use can be deposited into the internal cavity. The distal end of the orifice 328, in addition to providing cutting edge 332, is also defined by a radial flare 334 (FIG. 4A) that channels bone removed during use into the orifice 330.

Figure 5A:
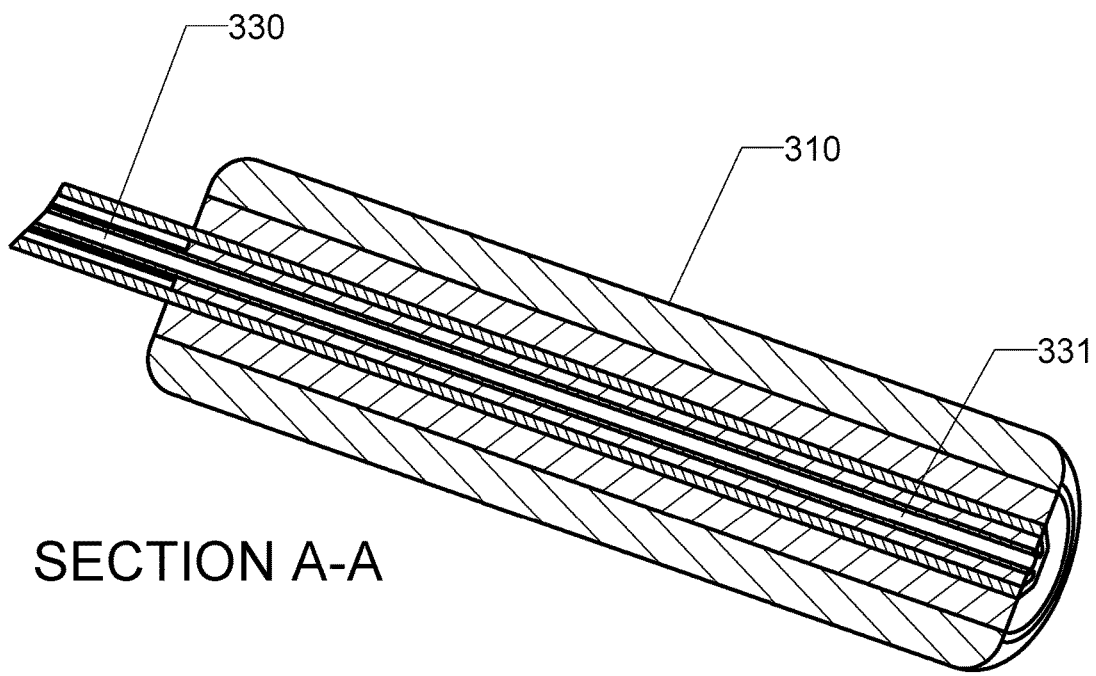
FIG. 5A is a perspective cross-sectional view of the osteotome of FIG. 4B.
Figure 5B:
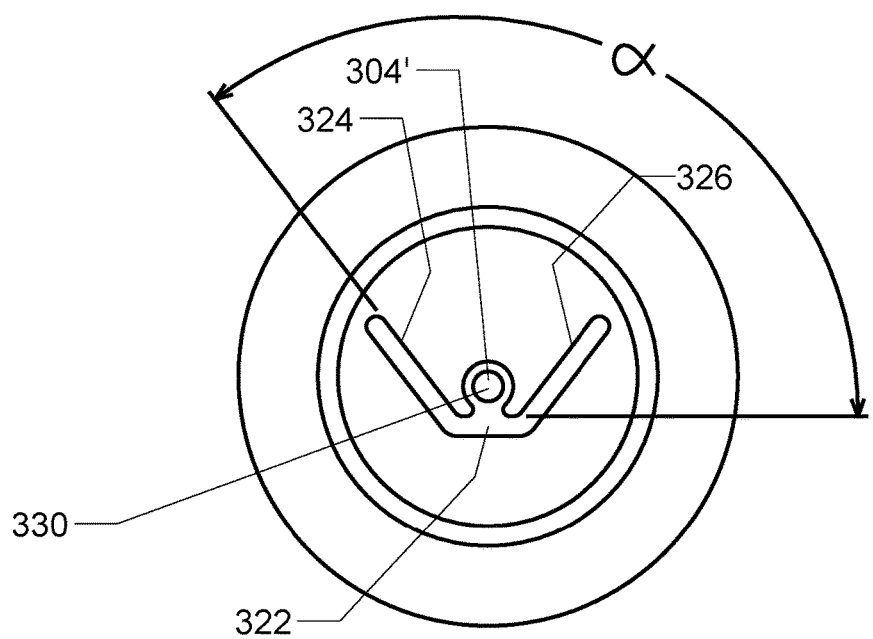
FIG. 5B is a bottom view of an osteotome in accordance with another exemplary embodiment of the subject disclosure.

As shown in FIGS. 5A and 5B, the guide 304' can alternatively be annular or cannulated, as opposed to substantially annular. In this exemplary embodiment, the orifice 330 is completely enclosed and in fluid communication with the internal cavity 331 of the handle 310. This distal end of the annular guide 304' can define the distally facing cutting edge 332, as described above in connection with FIG. 4A.

The blades and cutting edges of the subject disclosure (e.g., blade 118, 318, cutting edge 332) can be composed of metals or alloys having a suitable hardness, durability and processability, such as stainless steels. In certain embodiments, the entire shaft assembly is composed of stainless steel, with the blades machined or otherwise processed to provide a sharp distally facing cutting edge.

In accordance with another exemplary embodiment, the subject disclosure provides a shoulder arthroplasty system that includes a shoulder implant having a humeral stem and a perimeter wall, and the osteotome 100, 300.

FIGS. 6-9 depict an orthopedic implant 550 according to an exemplary embodiment of the subject disclosure applicable to the shoulder arthroplasty system. The orthopedic implant 550, which is not drawn to scale for purposes of illustration, includes a stem 534 having a groove 536. Solely for purposes of illustration, the orthopedic implant 550 will be described below in the context of a shoulder implant to be used in a shoulder arthroplasty surgery (e.g., TSA, RSA), though the subject disclosure is not limited thereto. For example, the subject disclosure applies equally to other orthopedic implants bearing a stem, e.g., a hip implant, tibial implant, intramedullary rods, and the like.

Figure 6:
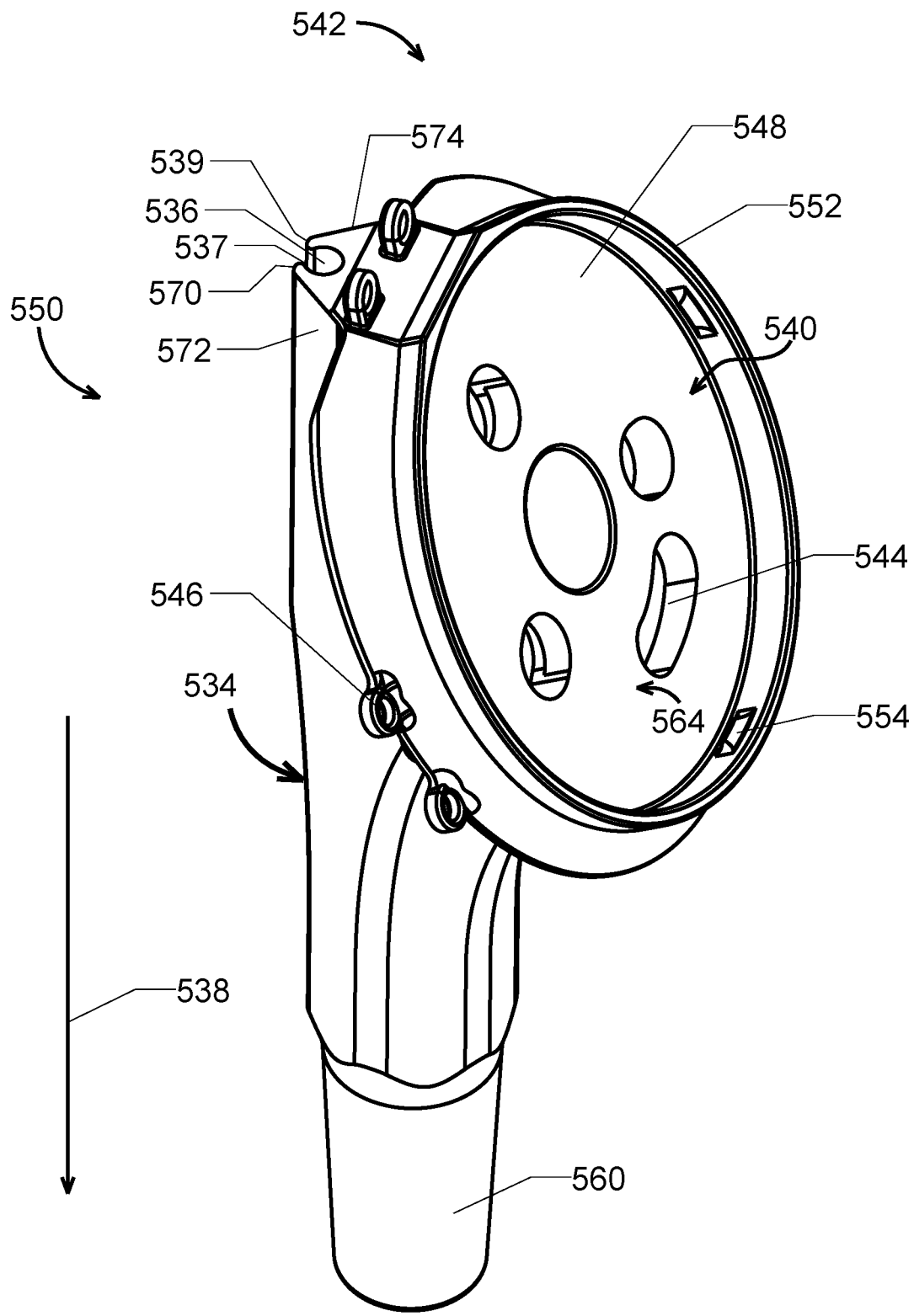
FIG. 6 is a perspective view of an orthopedic implant according to an exemplary embodiment of the subject disclosure.

The shoulder implant 550 is a humeral implant to be used in reverse shoulder arthroplasty. The shoulder implant includes a tray 540 located adjacent to a proximal end 542 of the implant. The tray 540 is configured as best shown in FIG. 6. The tray includes a circular plane 548 for receiving a polymer bearing component (not shown) and a circular ring 552 about a perimeter of the plane. The circular plane 548 includes a plurality of recesses 544 adapted to receive various features of the polymer bearing component which in turn receives a glenosphere (also not shown). A plurality of suture holes 546 are provided around the perimeter of the tray to provide an anchor for suturing procedures (e.g., suturing involving the greater tuberosity). Notches, detents or a similar retaining mechanism 554 are provided circumferentially about the circular ring 552 to assist in securing the polymer bearing component to the tray 540. In the particular embodiment shown in FIGS. 6-9, the tray 540 is integrally formed with the stem 534.

The stem 534 extends in the longitudinal direction 538 from the proximal end 542 of the implant 550. As shown best in FIG. 7, the stem 534 includes a proximal section 556 adjacent the tray 540. The proximal section 556 of the stem 534 further includes a threaded hole 562 adapted to receive a threaded shaft (not shown).

A middle section 558 of the stem proceeds from the proximal section 556. The middle section 558 has a narrowing profile as it proceeds from the proximal section 556, the profile being the widest along the proximal section where it forms a seat for an inferior portion 564 of the tray 540. The inferior portion 564 of the tray 540 further includes an overhanging portion 566 that is not supported by the stem 534. A distal portion 560 of the stem extends from the middle section 558 where the stem is defined by a circular or oval cross-sectional shaped shaft 568.

Figure 7:
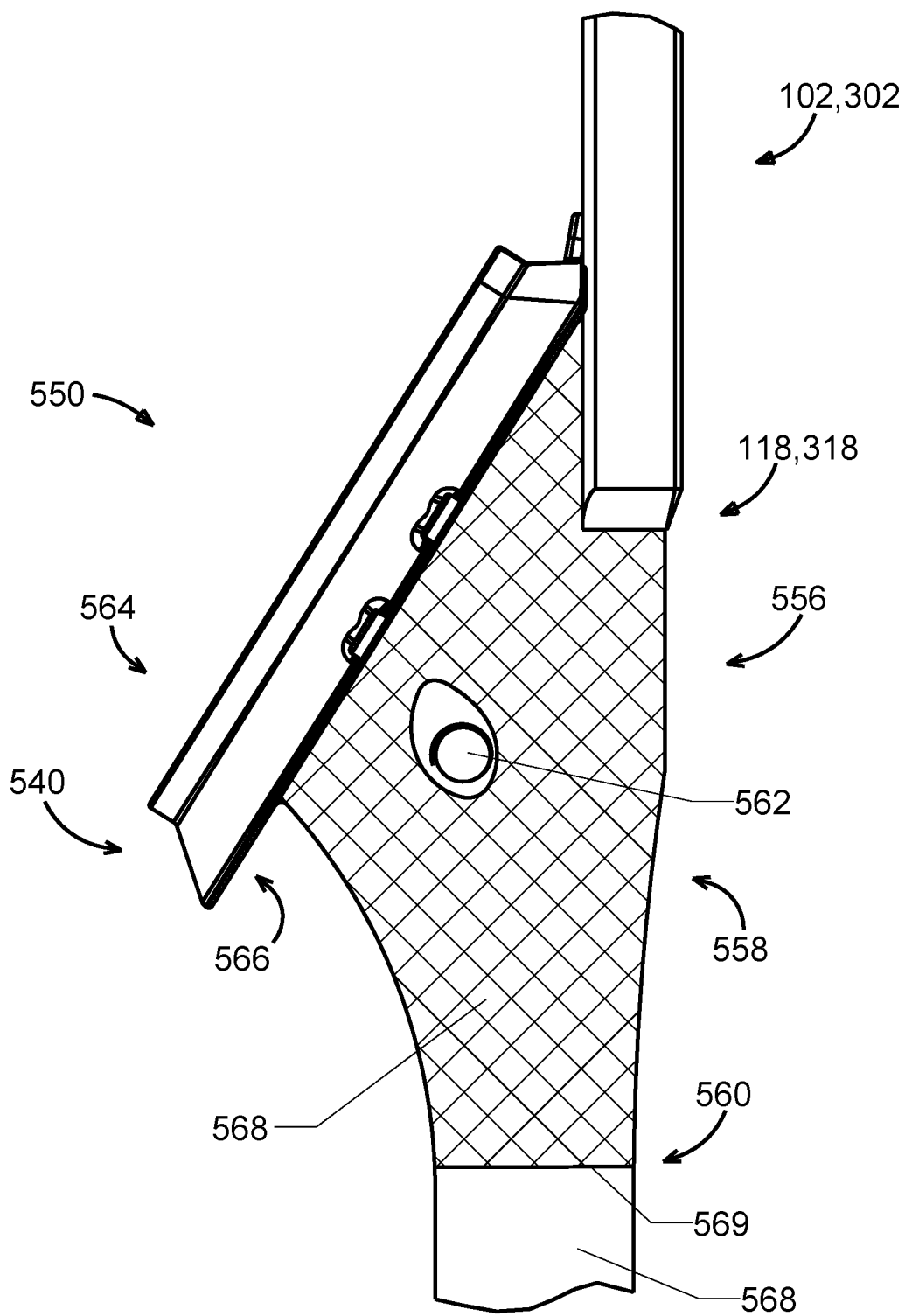
FIG. 7 is a side view of the osteotome of FIG. 1 or 3, being applied to the orthopedic implant of FIG. 6.

As shown in FIG. 7, the proximal section 556, the middle section 558 and a portion of the distal section 560 of the stem 534 can be provided with a porous or textured surface 568 to promote bone attachment, as represented by the diamond cross-hatching. In certain embodiments, the porous or textured surface does not extend an entire length of the stem 534 (e.g., there is an untextured portion of the distal section 560) so as to prevent the stem from being fractured when attempting to extract the implant during implant revision surgery. The amount of surface textured relative to an untextured portion of the stem can vary.

The total length of the stem 534 can also vary. In certain embodiments, the total length of the stem 534 is from about 2 inches to about 5 inches, or from about 2.5 inches to about 4.5 inches. In one embodiment, the stem 534 has a total length of about 3 inches.

The groove 536 can extend along a majority of the stem length. Alternatively, the groove can terminate about the proximal section 556 of the stem, or the middle section 558 of the stem, and/or not extend along a majority of the stem length.

As shown in FIG. 6, the groove 536 extends along a lateral side of the implant 550 opposite the side adjacent the tray. In this particular embodiment the grove extends along the stem, continuing in the longitudinal direction 538, through the middle section 558, and through a portion of the distal portion 560 of the stem. In sum, the groove expands along a majority of the stem length. The groove 536, in certain embodiments, maintains a constant cross-sectional shape throughout, or substantially throughout, the entire longitudinal length of the groove 536. In certain embodiments, a taper is provided adjacent a proximal end of the groove 536, to guide the osteotome therein.

The longitudinal length of the groove can vary, and can depend on, for example, the extent to which the implant is provided with a porous or textured surface. In this particular embodiment, the groove runs to about, or just beyond (e.g., $\frac{1}{16}^{th}$ or $\frac{1}{8}^{th}$ of an inch beyond) the distal reach 569 of the porous surface 568. The groove can extend a longitudinal length equal to or greater than a longitudinal length of the porous or textured surface.

The groove 536 has a longitudinal cross-sectional shape complementary to the longitudinal cross-sectional shape of the guide 104, 304 of the osteotome 100, 300. More particularly, the guide 104, 304 has a circular cross-sectional shape in these exemplary embodiments, the curvature of the circle defining outer flares. The shaft assembly 102, 302 is provided with a recessed portion or void 129, 329 around the outer flares, particularly in the area where the guide 104, 304 engages the first planar section 122, 322 of the blade so as to provide an area for the groove 536 to fittingly receive in a complementary fashion the male guide 104, 304.

The cross-sectional shape of the groove 536 correspondingly contains a circular longitudinal cross-sectional shape with lips 537, 539 shaped to fit within the void 129, 329 provided around the outward flares of the groove 536. In exemplary embodiments, the groove 536 receives the guide 104, 304 to form a dovetail connection in which movement of the osteotome 100, 300 is restricted to, and thus efficiently directed along the longitudinal direction of the stem 534, when the guide 104, 304 is engaged with the groove 534.

The particular cross-sectional shape of the groove 536 and the guide 104, 304 is described above for purposes of illustration and not limitation, as other configurations of the guide 104, 304 and groove 536 can be provided in order to provide, for example, a dovetail connection. For example, according to alternative embodiments of the subject disclosure, the guide can have a longitudinal cross-section of an oval guide 104' (FIG. 2E), square guide 104" (FIG. 2H), rectangle guide 104''' (FIG. 2I), trapezoid guide 104'''' (FIG. 2F), triangle guide 104''''' (FIG. 2G), or curve 104'''''' (FIG. 2J), with the groove having a corresponding longitudinal cross-sectional shape.

Referring back to FIG. 6, at the proximal end 542 of the shoulder implant 550, the groove is centered about, and dissects, a first perimeter wall section 570 of the implant, which runs from the proximal end 542 of the implant and extends in the longitudinal direction 538 of the stem along the proximal section 556 of the stem. A second perimeter wall section 572 of the implant and a third perimeter wall section 574 of the implant extend from the first perimeter wall section 570, these sections also being located along the perimeter of the proximal section 556 of the stem.

In certain embodiments, the second perimeter wall section 572 of the implant and/or the third perimeter wall section 574 of the implant extend from the first perimeter wall section 570 at an angle of about 125° to about 135°, or from about 128° to about 132° (e.g., 130°). Alternatively, the second perimeter wall section 572 and/or the third perimeter wall section 574 can extend from the first perimeter wall section 570, at an angle from about 90° to about 180°, or from about 110° to about 150° (e.g., 110°, 111°, 112°, 113°, 114°, 115°, 116°, 117°, 118°, 119°, 120°, 121°, 122°, 123°, 124°, 125°, 126°, 127°, 128°, 129°, 130°, 131°, 132°, 133°, 134°, 135°, 136°, 137°, 138°, 139°, 140°, 141°, 142°, 143°, 144°, 145°, 146°, 147°, 148°, 149°, or 150°).

The orientation of the blade 118, 318 of the osteotome 100, 300 corresponds to the orientation of the implant 550, and more particularly the orientation of the proximal section 556 of the stem 534. According to an exemplary embodiment, the orientation of the first planar section 122, 322, the second planar section 124, 324, and the third planar section 126, 326 of the blade 118 corresponds to the orientation of the first perimeter wall section 570, the second perimeter wall section 572, and the third perimeter wall section 574 of the implant 550. Further, in certain exemplary embodiments, such as shown in FIG. 7, the blade 118, 318, and the guide 104, 304 of the shaft assembly 102, 302 are oriented with respect to each other such that the cutting blade 118, 318 engages the first perimeter wall section 570, the second perimeter wall section 572, and the third perimeter wall section 574 of the implant 550 when the guide 104, 304 is engaged with the groove 536, e.g., in a complimentary fitting manner.

Figure 8:
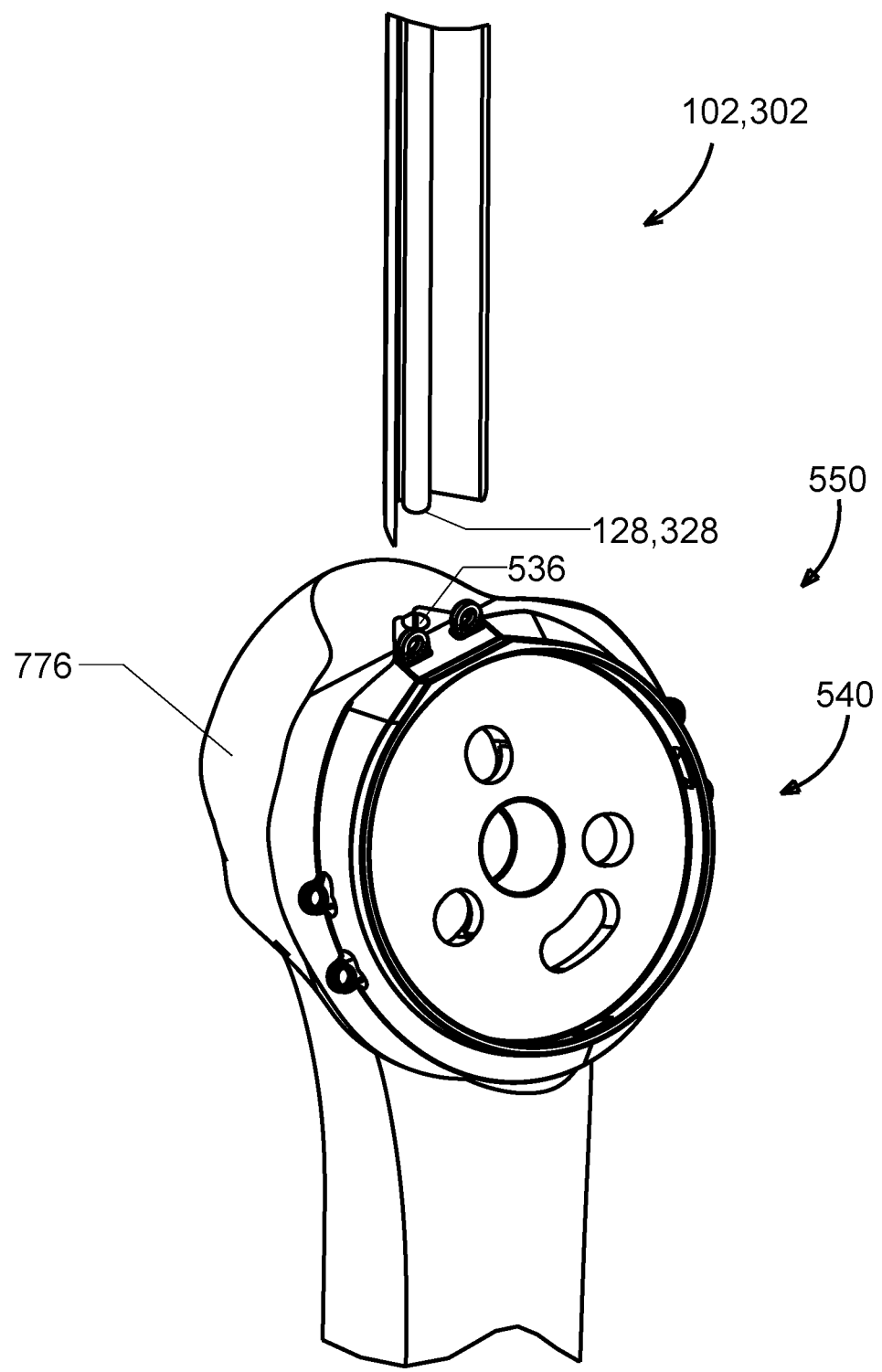
FIG. 8 is a perspective view of the osteotome of FIG. 1 and the orthopedic implant according to FIG. 6 implanted in a humerus.
Figure 9:
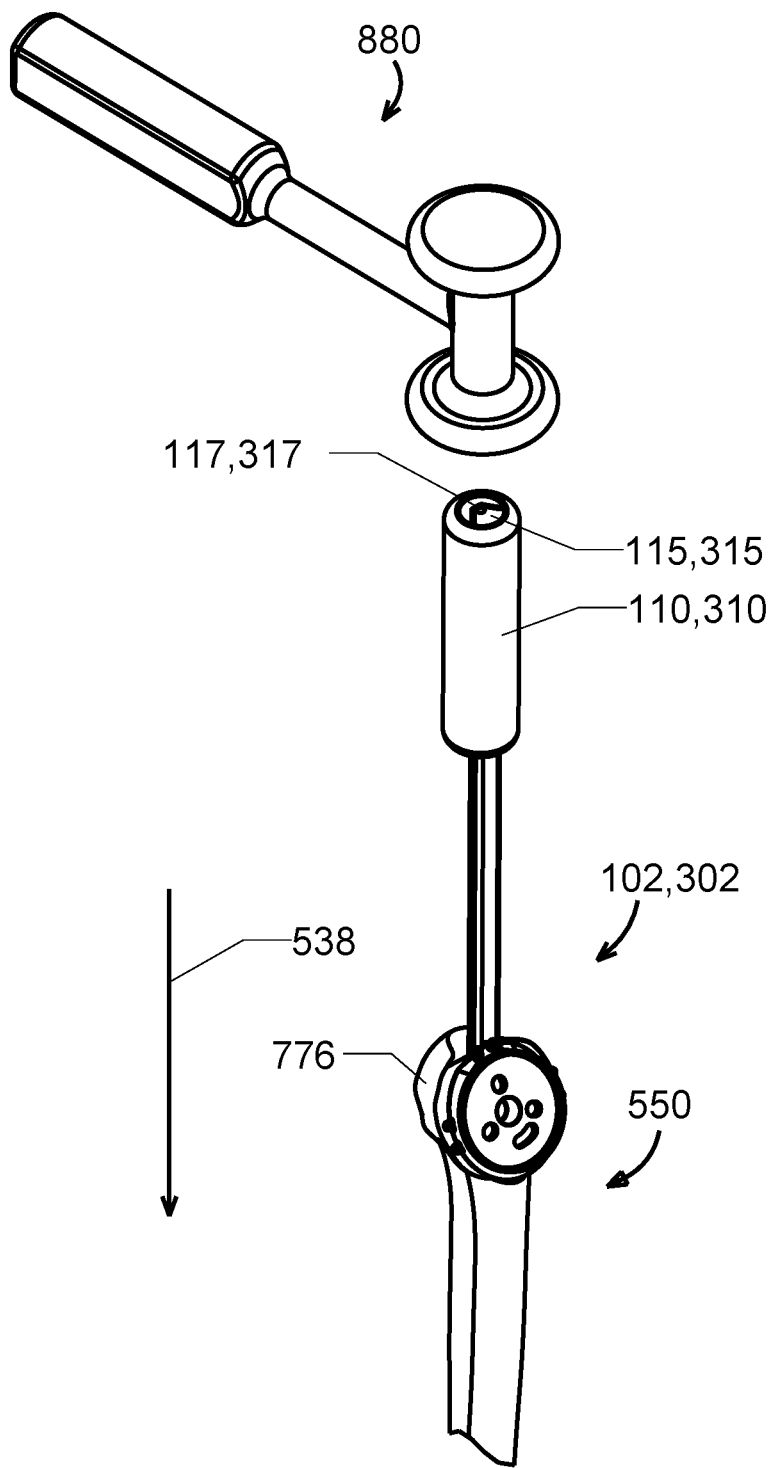
FIG. 9 is a perspective view of the osteotome of FIG. 1 or 3 and the orthopedic implant according to FIG. 6 in accordance with the subject disclosure.

Operation of the osteotome 100, 300 will be described in connection with FIGS. 8-9, which depict the orthopedic implant 550 implanted in a humerus 776 of a subject undergoing a shoulder revision procedure. An operator will grasp the handle 110, 310, position the shaft assembly 102, 302 about a proximal end to the humerus 776, and insert the distal end of the guide 128, 328 into the groove 536 of the implant. Once the distal end 128, 328 of the guide 104, 304 is inserted into the groove 536, the cutting blade 118, 318 engages the periphery of the proximal section of the stem and is positioned to remove bone ingrowth that has occurred along the surface of the implant 550 and/or into the groove. An operator could manually push or otherwise direct the shaft assembly 102, 302 downward (as oriented in FIG. 9) in the longitudinal direction 538 of the stem 534. Alternatively, an operator could strike the striking surface 115, 315 of the osteotome with a surgical hammer 880 to direct the shaft assembly 102, 302 in longitudinal direction 538 of the stem 534. The foregoing advantageously provides a close and guided direction of the travel of an osteotome for the removal of an implant at the implant bone interface.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the subject disclosure as defined by the appended claims.

The invention claimed is:

1. An osteotome comprising:
a shaft assembly that includes:
a guide extending in a longitudinal direction of the shaft assembly, and
a blade adjacent to and connected to the guide along an entire longitudinal length of the guide, the blade including a distally facing cutting edge.

2. The osteotome of claim 1, wherein the guide is a substantially cylindrical guide.

3. The osteotome of claim 1, wherein the guide is a substantially annular guide.

4. The osteotome of claim 1, wherein the guide is an elongated guide having a longitudinal cross-section of a circle, oval, square, rectangle, trapezoid, triangle, or curve.

5. The osteotome of claim 1, wherein the blade has a first planar section connected to the guide along an entire longitudinal extent of the guide.

6. The osteotome of claim 5, wherein the blade further comprises:
a second planar section extending from a first lateral end of the first planar section over an entire longitudinal extent of the first planar section; and
a third planar section extending from a second lateral end of the first planar section opposite the first lateral end of the first planar section over the entire longitudinal extent of the first planar section.

7. The osteotome of claim 6, wherein:
the second planar section extends from the first planar section at an angle from about 90° to about 150°, and
the guide is between the second planar section and the third planar section.

8. The osteotome of claim 6, wherein the third planar section extends from the first planar section about 90° to about 150°.

9. The osteotome of claim 1, wherein the blade is an elongated blade.

10. The osteotome of claim 9, wherein the elongated blade has a longitudinal cross-section of a curve, substantially U-shaped, substantially V-shaped, substantially trapezoidal shaped.

11. The osteotome of claim 1, further comprising a handle connected to a proximal end of the shaft assembly.

12. The osteotome of claim 11, wherein the handle includes a striking surface.

13. The osteotome of claim 12, wherein the striking surface is a substantially planar proximally facing striking surface.

14. The osteotome of claim 11, wherein the handle includes an internal cavity, and wherein the guide includes a through hole extending along a longitudinal direction of the guide and in fluid communication with the internal cavity.

15. A shoulder implant comprising:
a humeral stem having a groove extending from a proximal end of the stem, and along a longitudinal axis of the stem towards a distal end of the stem, wherein the groove has an open end at the proximal end of the stem; and
wherein the open end of the groove is opposite a tray portion at the proximal end of the stem, the tray portion configured to receive a bearing component of the shoulder implant.

16. The orthopedic implant of claim 15, wherein the groove extends along a majority of the stem length.

17. A shoulder arthroplasty system comprising:
a shoulder implant that includes:
- a humeral stem having a groove extending along a longitudinal axis of the humeral stem, and
- a perimeter wall adjacent the groove; and an osteotome comprising a shaft assembly that includes:
- a guide extending in a longitudinal direction of the shaft assembly, and
- a blade adjacent connected to the guide along an entire longitudinal length of the guide, and including a distally facing cutting edge,
- wherein the guide is shaped to engage with the perimeter wall.

18. The shoulder arthroplasty system of claim 17, wherein the groove is complementary shaped to the guide for receiving the guide therein.

19. The shoulder arthroplasty system of claim 17, wherein the groove is formed within a wall having a first peripheral wall section and a second peripheral wall section about lateral sides of the groove.

* * * * *